(12) United States Patent
Shoshan

(10) Patent No.: US 10,004,429 B2
(45) Date of Patent: Jun. 26, 2018

(54) METHOD AND SYSTEM FOR MEASURING A PATH LENGTH USING A HANDHELD ELECTRONIC DEVICE

(71) Applicant: My Size Israel 2014 Ltd., AirportCity (IL)

(72) Inventor: Oded Shoshan, Tel Aviv (IL)

(73) Assignee: My Size Israel 2014 Ltd., Airport City (IL)

( * ) Notice: Subject to any disclaimer, the term of this patent is extended or adjusted under 35 U.S.C. 154(b) by 125 days.

(21) Appl. No.: 15/112,484

(22) PCT Filed: Jan. 6, 2015

(86) PCT No.: PCT/IL2015/050022
§ 371 (c)(1),
(2) Date: Jul. 19, 2016

(87) PCT Pub. No.: WO2015/111038
PCT Pub. Date: Jul. 30, 2015

(65) Prior Publication Data
US 2016/0331276 A1  Nov. 17, 2016

Related U.S. Application Data

(60) Provisional application No. 61/929,635, filed on Jan. 21, 2014.

(51) Int. Cl.
*A61B 5/103* (2006.01)
*A61B 5/107* (2006.01)
(Continued)

(52) U.S. Cl.
CPC ............ *A61B 5/1072* (2013.01); *A61B 5/112* (2013.01); *A61B 5/6898* (2013.01); *G01B 21/02* (2013.01);
(Continued)

(58) Field of Classification Search
CPC .................................. A61B 5/107; G01B 3/12
(Continued)

(56) References Cited

U.S. PATENT DOCUMENTS 8,079,258 B1  12/2011 Sapuppo
9,799,068 B2 * 10/2017 Zigdon .............. G06Q 30/0641
(Continued)

FOREIGN PATENT DOCUMENTS

CN  1713657 A  12/2005
CN  201011724 Y  1/2008
(Continued)

OTHER PUBLICATIONS 4. https://developer.android.com/guide/topics/sensors/sensors_overview.html—Dec. 12, 2013.
(Continued)

*Primary Examiner* — G. Bradley Bennett
(74) *Attorney, Agent, or Firm* — Wiggin and Dana LLP; Gregory S. Rosenblatt; Andrew D. Bochner

(57) ABSTRACT

The present disclosure provides a method for measuring a path length using a handheld electronic device comprising: repeatedly tumbling forward the handheld electronic device so as to cover the path to be measured; sensing a rotational change of the handheld electronic device; counting fractional increments of revolution of the handheld electronic device with respect to a starting position; and estimating the path length based on the counted fractional increments of revolution.

37 Claims, 5 Drawing Sheets

(51) Int. Cl.
  *G01B 21/02* (2006.01)
  *A61B 5/00* (2006.01)
  *A61B 5/11* (2006.01)
  *G01C 22/00* (2006.01)
  *G01C 19/00* (2013.01)
  *G06F 1/16* (2006.01)

(52) U.S. Cl.
  CPC ........... *G01C 19/00* (2013.01); *G01C 22/006* (2013.01); *G06F 1/1694* (2013.01); *A61B 2503/12* (2013.01)

(58) Field of Classification Search
  USPC .......................................... 33/512, 772–782
  See application file for complete search history.

(56) References Cited

U.S. PATENT DOCUMENTS

| | | | |
|---|---|---|---|
| 2003/0145480 A1 | 8/2003 | Endo | |
| 2004/0068886 A1* | 4/2004 | Trout | G01B 3/12 33/773 |
| 2006/0267791 A1 | 11/2006 | Chiang | |
| 2008/0060210 A1* | 3/2008 | Trout | G01B 3/12 33/773 |
| 2009/0318200 A1 | 12/2009 | Huang | |
| 2016/0242695 A1* | 8/2016 | Ajima | G01B 21/20 |
| 2016/0303341 A1* | 10/2016 | Niccol | A61B 5/1072 |
| 2017/0370687 A1* | 12/2017 | Lai | G01B 3/12 |

FOREIGN PATENT DOCUMENTS

| | | |
|---|---|---|
| CN | 201910849 U | 7/2011 |
| CN | 201947342 U | 8/2011 |
| CN | 202533013 U | 11/2012 |
| CN | 202589531 U | 12/2012 |
| CN | 102927942 A | 2/2013 |
| CN | 102988054 A | 3/2013 |
| CN | 103209261 A | 7/2013 |
| KR | 20050083081 A | 8/2005 |
| KR | 100652685 B | 12/2006 |
| KR | 100722435 B | 1/2007 |
| KR | 100890252 B1 | 3/2009 |
| KR | 100924826 B | 11/2009 |
| KR | 20130052159 A | 5/2013 |
| KR | 20130081037 A | 7/2013 |
| WO | 201002033 A | 1/2010 |
| WO | 2012/110828 A1 | 8/2012 |
| WO | 2012/172568 A1 | 12/2012 |
| WO | 2013/032041 A1 | 3/2013 |
| WO | 2013/059599 A1 | 4/2013 |
| WO | 2013/108260 A1 | 7/2013 |
| WO | 13175228 A1 | 11/2013 |

OTHER PUBLICATIONS 5. https://he.wikipedia.org/wiki/D7%A7%D7%95%D7%91%D7%A5:GraphesMRUA.png—Dec. 12, 2007.
6. https://play.google.com/store/apps/details?id=kr.sira.measure—Dec. 10, 2013.
7. http://ttic.uchicago.edu/~rurtasun/courses/CV/lecture08.pdf—Feb. 5, 2013.
Clickconnect GmbH, Rotation Ruler, App Store for iOS Devices, Available since Mar. 24, 2011.

* cited by examiner

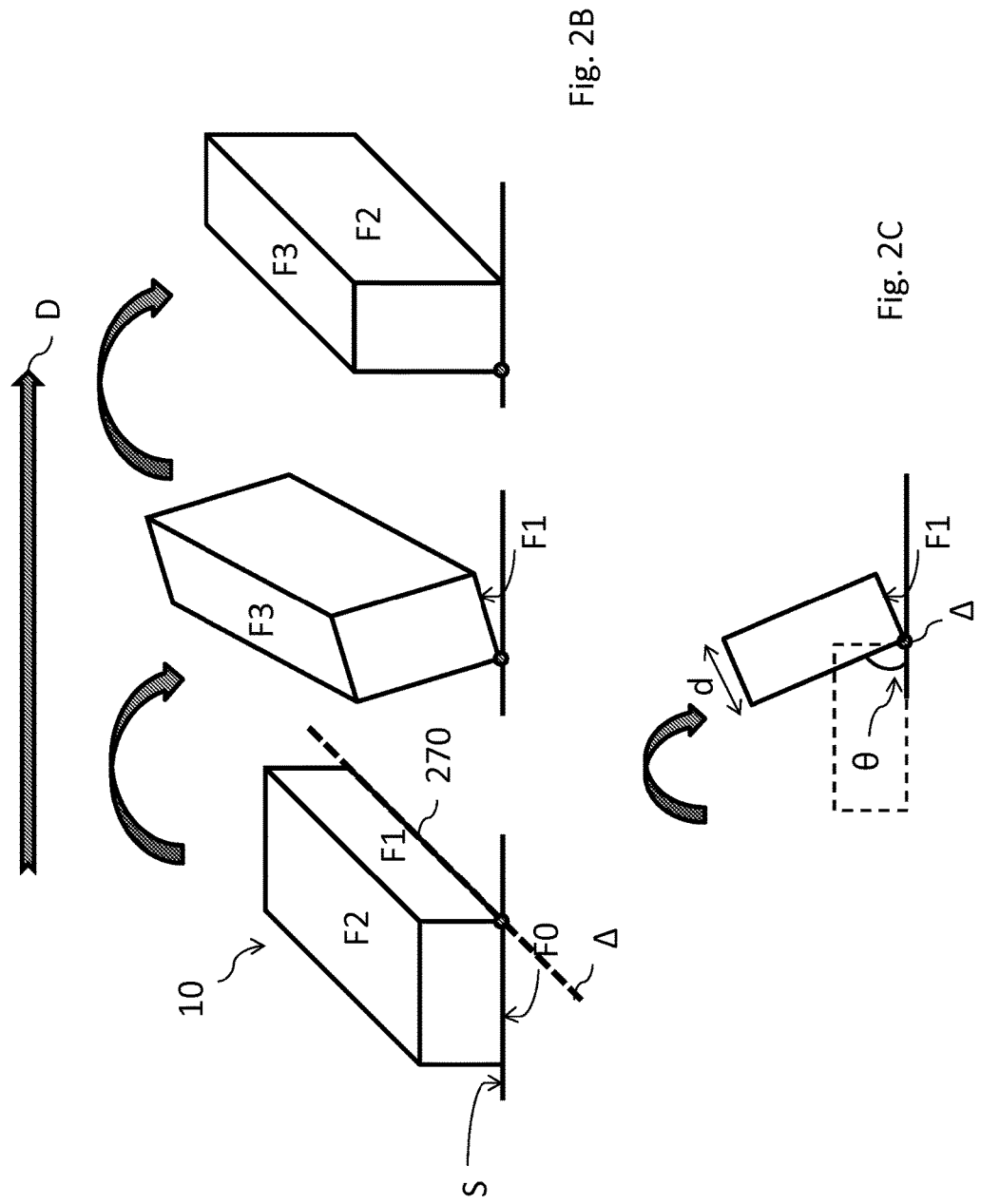

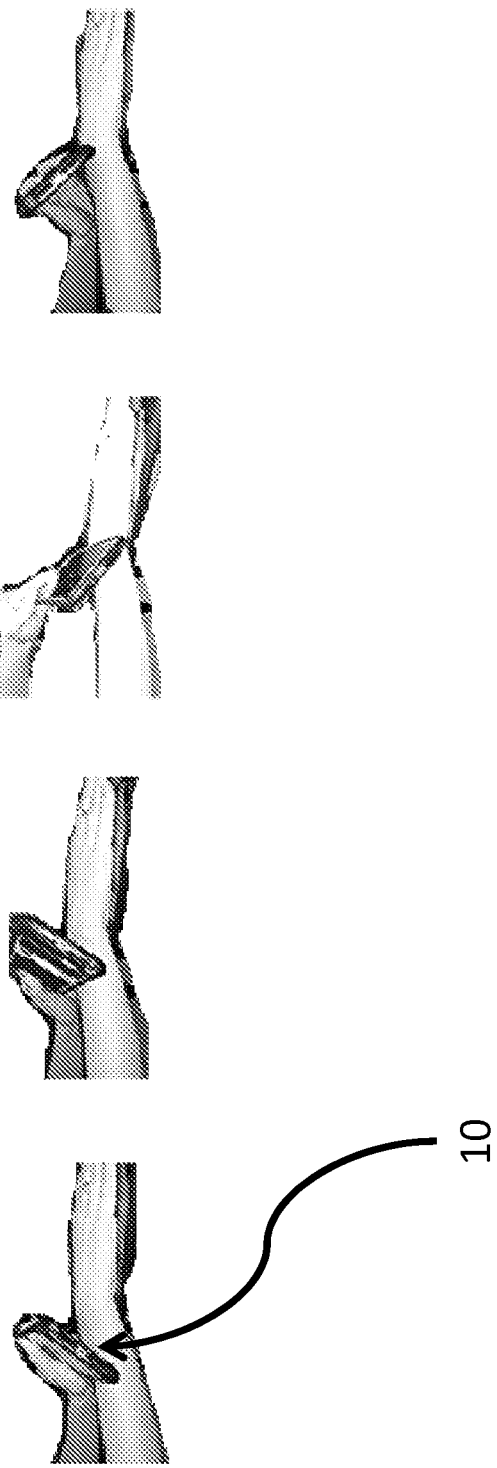

METHOD AND SYSTEM FOR MEASURING A PATH LENGTH USING A HANDHELD ELECTRONIC DEVICE

CROSS REFERENCE TO RELATED APPLICATIONS

This application is a United States national application filed pursuant to 35 USC § 371, claiming benefit of international PCT Application No. PCT/IL2015/050022, entitled "METHOD AND SYSTEM FOR MEASURING A PATH LENGTH USING A HANDHELD ELECTRONIC DEVICE" and filed on Jan. 6, 2015, which claims the benefit of U.S. Provisional Patent Application No. 61/929,635, which was filed on Jan. 21, 2014. The disclosures of PCT/IL2015/050022 and 61/929,635 are incorporated by reference herein in their entirety.

FIELD OF THE PRESENT DISCLOSURE

The present disclosure relates to the field of measuring. More specifically the present disclosure relates to a method and system for measuring a path length using a handheld electronic device.

BACKGROUND

The growth of electronic commerce or e-commerce allows for the availability of online shopping. Online shopping allows a user to view and purchase an item online, over the Internet, and in some examples, via a web browser on a phone, personal computer, television and/or other Internet connected device without trying the item on or without determining how well it will fit.

A subset of online commerce is mobile commerce (m-commerce) where a user may specifically employ a mobile device for viewing and purchasing an item. Payments can be in the form of credit, bank transfers, credit cards, gift cards, money orders, and or other cash alternatives including Bitcoin and similar Internet currencies.

E-commerce, m-commerce and other forms of online shopping and commerce also allow a retailer, distributor or another component of a supply chain for an item to broaden their market, selling items to markets where sizing information may not necessarily be transferable, given different measurements or different average body sizes.

Consumers may not necessarily interact with a retailer online. In some examples, a consumer may search for an item via a search engine, a shopping search engine, and/or aggregators. Consumers may, in some examples, use one or a plurality of portals to conduct e-commerce.

GENERAL DESCRIPTION

The present disclosure provides a method and a system for measuring a path length using a handheld electronic device. The path length may substantially extend in one path direction.

The handheld electronic device may be configured for estimating a rotational change (orientation variation) of the handheld electronic device with respect to a reference position. In order to do so, the handheld electronic device may be provided with orientation sensors such as a gyroscope and/or an accelerometer.

In some embodiments, the handheld electronic device may have a substantially rectangular cuboid shape. Edges of the handheld electronic device may substantially define an orthogonal referential comprising three orthogonal axis X, Y, Z of the handheld electronic device as illustrated on FIG. 1. The three orthogonal axes X, Y, Z of the handheld electronic device may enable to define three types of orthogonal planes: thickness section planes perpendicular to Z, for example (X,Y); height section planes perpendicular to X, for example (Y, Z) and width section planes perpendicular to Y, for example (X, Z).

In some embodiments, the handheld electronic device may be rolled over the path to be measured. In other words, the handheld electronic device may be repeatedly tumbled forward so as to cover the path to be measured. A reference position of the handheld electronic device may be a starting position in which the handheld electronic device is positioned on the path surface. Preferably, in the starting position, an edge of the handheld electronic device may be perpendicular to the path direction in which the path to be measured extends and in which the handheld electronic device is to be tumbled forward.

More precisely, the handheld electronic device may be pivoted forward around its forward bottom edge, wherein a bottom orientation may be defined with respect to a support surface on which the handheld electronic device is supported (the path surface) and a forward orientation may be defined with respect to the path direction. The handheld electronic device may be tumbled along the path such that successive rolling faces of the handheld electronic device successively cover the path to be measured, wherein successive rolling faces refer to adjacent faces of the handheld electronic device such that a vector product of vectors perpendicular to said faces is substantially perpendicular to the path direction. It is to be noted that in the tumbling movement, the faces of the handheld electronic device may be laid down on the path and enter into contact with the path to be measured when a remaining path length to measure is longer than a handheld electronic device extension. In some embodiments, when the handheld electronic device would extend beyond the end of the path if the handheld electronic device is laid on the path (i.e. a remaining path length is shorter than the handheld electronic device extension e.g. either a thickness, a width or a height depending on how the device is tumbled), then the handheld electronic device is swung around its forward bottom edge until a projection of an edge of the handheld electronic device on the path reaches the end of the path.

Similarly, the movement of the handheld electronic device may be described by the handheld electronic device being rolled over the path such that a circumference (perimeter) of the handheld electronic device along one of the section planes covers the path to be measured. In other words, the term "rotate along" may be understood as a series of successive rotations, wherein each rotation of the series may be performed around a forward bottom edge of the handheld electronic device. A corresponding series of rotation axes may be collinear to each other and perpendicular to the path direction. In fact, the handheld electronic device may be used as a kind of measuring wheel, wherein a frame of the handheld electronic device serves as a (in general not circular) wheel.

The orientation sensors may enable to count fractional increments of revolution of the handheld electronic device thereby enabling to derive the path length covered by the handheld electronic device as a function of its width, height and/or thickness depending on how the device is tumbled. In the following, a revolution of the handheld electronic device may refer to a 360 degrees rotation.

The handheld electronic device may preferably be moved over the path without slipping. In some embodiments, the handheld electronic device may be configured to detect and optionally to also correct a slipping in the tumbling movement by detecting an irregular rotation movement. For example, the handheld electronic device may detect an excess acceleration in a given direction. Based on the excess acceleration, the handheld electronic device may be configured to assess a slipping of the handheld electronic device and take into account such slipping in the path measurement.

Therefore, the present disclosure discloses a method for measuring a path length using a handheld electronic device comprising: repeatedly tumbling forward the handheld electronic device so as to cover the path to be measured; sensing a rotational change of the handheld electronic device; counting fractional increments of revolution of the handheld electronic device with respect to a starting position; and estimating the path length based on the counted fractional increments of revolution.

In some embodiments, each fractional increment is associated with a corresponding perimeter projection part of the handheld electronic device and the path length is estimated by summing said perimeter projection parts.

In some embodiments, a revolution of the handheld electronic device is divided into a predetermined number of fractional increments and wherein counting the fractional increments comprises updating a counter comprising a bit array of a corresponding predetermined number of bits.

In some embodiments, the sensing of the rotational change is performed repeatedly while the handheld electronic device is tumbled forward.

In some embodiments, the perimeter projection parts are based on an extension of the handheld electronic device in a section plane perpendicular to a rotation axis of the handheld electronic device.

In some embodiments, the method further comprises detecting a slipping movement of the handheld electronic device based on the sensed rotational change and correcting the estimated path length using the detected slipping.

In some embodiments, the method further comprises a step of auto-correction of the counted fractional increments of revolution of the handheld electronic device.

In some embodiments, the fractional increments of revolution correspond to a rotation of the handheld electronic device of 22.5 degrees each.

In some embodiments, a user conducts said method via voice commands.

In some embodiments, said handheld electronic device is a smartphone.

In some embodiments, said path is a body part.

In some embodiments, the sum of the perimeter projection parts corresponding to a revolution of the handheld electronic device approximates a perimeter of a section of the handheld electronic device in a plane perpendicular to a rotation axis direction.

In some embodiments, the measuring of a path length using a handheld electronic device is configurable for use in e-commerce.

In some embodiments, the sensing of the rotational change is performed continuously.

In another aspect, the present disclosure provides one or more non-transitory computer-readable media (or computer program also referred to as computer program product) storing computer-readable instructions that, when executed by a handheld electronic device repeatedly tumbled forward so as to cover a path to be measured, cause the handheld electronic device to measure the path length by: sensing a rotational change of the handheld electronic device; counting fractional increments of revolution of the handheld electronic device with respect to a reference position; and estimating the path length based on the counted fractional increments of revolution.

In some embodiments, each fractional increment is associated with a corresponding perimeter projection part of the handheld electronic device and the path length is estimated by summing said perimeter projection parts.

In some embodiments, a revolution of the handheld electronic device is divided into a predetermined number of fractional increments and wherein counting the fractional increments comprises updating a counter comprising a bit array of a corresponding predetermined number of bits.

In some embodiments, the computer product further comprises instructions for detecting a slipping movement of the handheld electronic device based on the sensed rotational change and correcting the path length estimated based on the detected slipping.

In some embodiments, the sensing of the rotational change is performed repeatedly while the handheld electronic device is tumbled forward.

In some embodiments, the computer program comprises instructions for performing an auto-correction of the counted fractional increments of revolution of the handheld electronic device.

In some embodiments, the fractional increments of revolution correspond to a rotation of the handheld electronic device of 22.5 degrees each.

In some embodiments, the computer program product further causes the handheld electronic device to respond to voice commands to measure a path length.

In some embodiments, the computer program product is configurable (configured) to run on a smartphone.

In some embodiments, the computer program product is configurable (configured) to measure a body part.

In some embodiments, the computer program product is configurable (configured) to be used in e-commerce.

In another aspect, the present disclosure provides a system for measuring a measuring a path length comprising: a handheld electronic device being intended to be tumbled forward so as to cover a path length to be measured, the handheld electronic device comprising: one or a plurality of sensors capable of sensing a rotational change of the handheld electronic device; and one or a plurality of processors configured for: sensing a rotational change of the handheld electronic device using the one or plurality of sensors; counting fractional increments of revolution of the handheld electronic device with respect to a starting position; and estimating a path length based on the counted fractional increments.

In some embodiments, each fractional increment is associated with a corresponding perimeter projection part of the handheld electronic device and estimating the path length is performed by summing said perimeter projection parts.

In some embodiments, the system is further configured for detecting a slipping movement of the handheld electronic device based on the sensed rotational change and correcting the path length estimated based on the detected slipping.

In some embodiments, the sensing of the rotational change is performed repeatedly while the handheld electronic device is tumbled forward.

In some embodiments, said one or a plurality of processors is configured to automatically perform a correction of the counted fractional increments.

In some embodiments, the fractional increments of revolution correspond to a rotation of the handheld electronic device of 22.5 degrees each.

In some embodiments, said one or a plurality of processors is configured for responding to voice commands.

In some embodiments, said one or a plurality of sensors and said one or plurality of processors is in a smartphone.

In some embodiments, the system is configurable (configured) to measure a body part.

In some embodiments, the system is configurable (configured) to be used in e-commerce.

According to another aspect of the presently disclosed subject matter there is provided in accordance with some embodiments of the present disclosure a method for measuring a path length using a continuous rotation comprising sensing at least a first rotation of a device along a path length, dividing the at least first rotation of the device into sectors, each sector being a portion of an angle of rotation of the device, wherein the sum of all traversed sectors at least approximates the angle of rotation of the device, counting said sectors to determine a completion of the at least first rotation wherein a full rotation of the device represents a measurement, said measurement at least approximating a length, the length equal to a multiple of a width and a multiple of a depth of the device, and/or counting said sectors to calculate an incompletion of the at least first rotation or a subsequent rotation wherein an incomplete rotation represents a measurement less than the measurement represented by the full rotation and wherein said measurement less than the measurement represented by the full rotation is calculated as a function of the angle of rotation, and calculating the path length by summing the measurements represented by the full rotations of the device and the measurements represented by the incomplete rotations of the device.

Furthermore, in accordance with some embodiments of the present disclosure, erroneously non-sensed portions of an angle of rotation are automatically corrected.

Furthermore, in accordance with some embodiments of the present disclosure, the at least first rotation is divided equally into sectors.

Furthermore, in accordance with some embodiments of the present disclosure, the at least first rotation is divided equally into 16 sectors of 22.5 degrees each.

Furthermore, in accordance with some embodiments of the present disclosure, a user conducts said method via voice commands.

Furthermore, in accordance with some embodiments of the present disclosure, said device is a smartphone.

Furthermore, in accordance with some embodiments of the present disclosure, said path is a body part.

Furthermore, in accordance with some embodiments of the present disclosure, the measurement represented by a full rotation of the device approximates at least a span of two widths of the device and two depths of the device.

Furthermore, in accordance with some embodiments of the present disclosure, measuring of a path length using a continuous rotation is configurable for use in e-commerce.

There is further provided, in accordance with some embodiments of the present disclosure, one or more non-transitory computer-readable media storing computer-readable instructions that, when executed by a device, cause the device to measure a path length using a continuous rotation according to the method previously described.

There is further provided, in accordance with some embodiments of the present disclosure, a system for measuring a path length using a continuous rotation comprising one or a plurality of sensors for sensing at least a first rotation of a device along a path length and one or a plurality of processors, the processors configurable to divide the at least a first rotation of the device into sectors, each sector being a portion of an angle of rotation of the device, wherein cumulative sectors at least approximate the angle of rotation of the device, count said sectors to determine a completion of the at least first rotation wherein a full rotation of the device represents a measurement, said measurement at least approximating a length, the length equal to a multiple of a width and a multiple of a depth of the device, and/or count said sectors to calculate an incompletion of the at least first rotation or a subsequent rotation wherein an incomplete rotation represents a measurement less than the measurement represented by the full rotation and wherein said measurement less than the measurement represented by the full rotation is calculated as a function of the angle of rotation, and calculate the path length by summing the measurements represented by the full rotations of the device and the measurements represented by the incomplete rotations of the device.

Furthermore, in accordance with some embodiments of the present disclosure, there is provided a system wherein said one or a plurality of processors is configurable to automatically correct erroneously non-sensed portions of an angle of rotation.

Furthermore, in accordance with some embodiments of the present disclosure, there is provided a system wherein said one or a plurality of processors is configurable to divide the at least first rotation equally into sectors.

Furthermore, in accordance with some embodiments of the present disclosure, there is provided a system wherein said one or a plurality of processors is configurable to divide the at least first rotation equally into 16 sectors of 22.5 degrees each.

Furthermore, in accordance with some embodiments of the present disclosure, there is provided a system wherein said one or a plurality of processors is configurable to respond to voice commands.

Furthermore, in accordance with some embodiments of the present disclosure, there is provided a system wherein said one or a plurality of sensors and said one or a plurality of processors are in a smartphone.

Furthermore, in accordance with some embodiments of the present disclosure, there is provided a system which is configurable to measure a body part.

Furthermore, in accordance with some embodiments of the present disclosure, there is provided a system which is configurable to be used in e-commerce.

BRIEF DESCRIPTION OF THE DRAWINGS

In the drawings and descriptions set forth, identical reference numerals indicate those components that are common in different drawings.

Elements in the drawings are not necessarily drawn to scale. It should be noted that the Figures are given as examples only and in no way limit the scope of the invention. Like components are denoted by like reference numerals.

Figure 1:
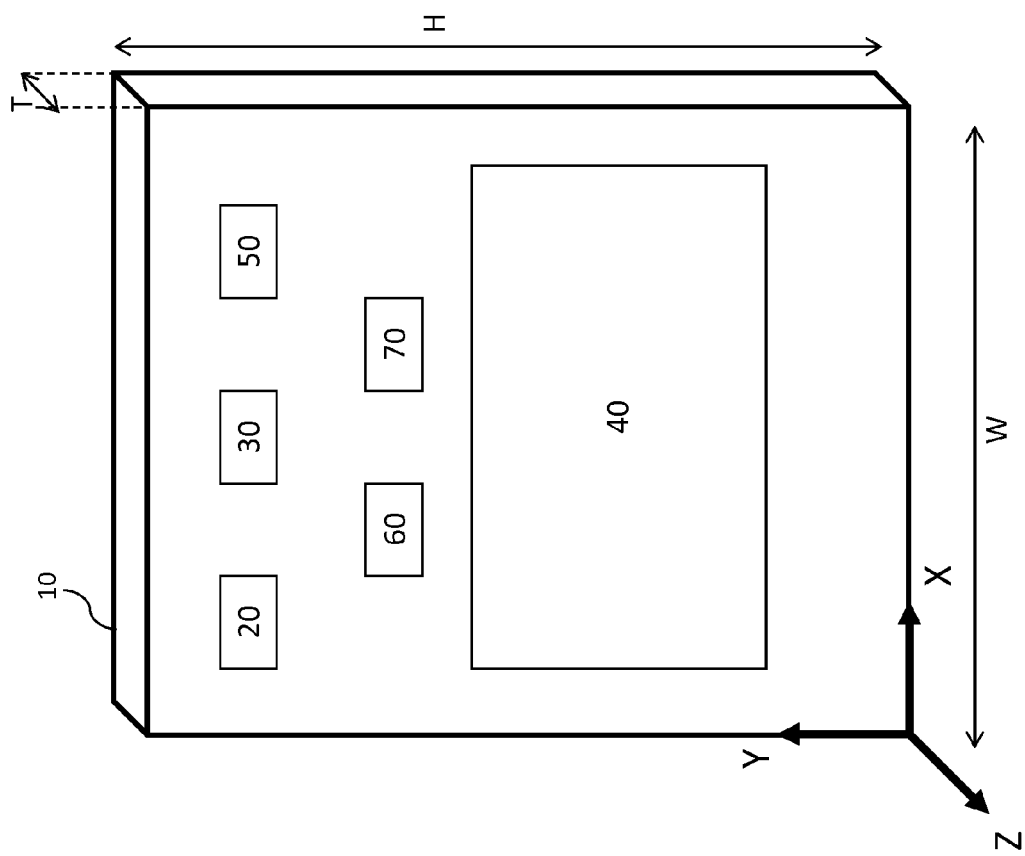

For example, the dimensions of some of the elements may be exaggerated relative to other elements for clarity. Further, where considered appropriate, reference numerals may be repeated among the figures to indicate corresponding or analogous elements.

Figure 2A:
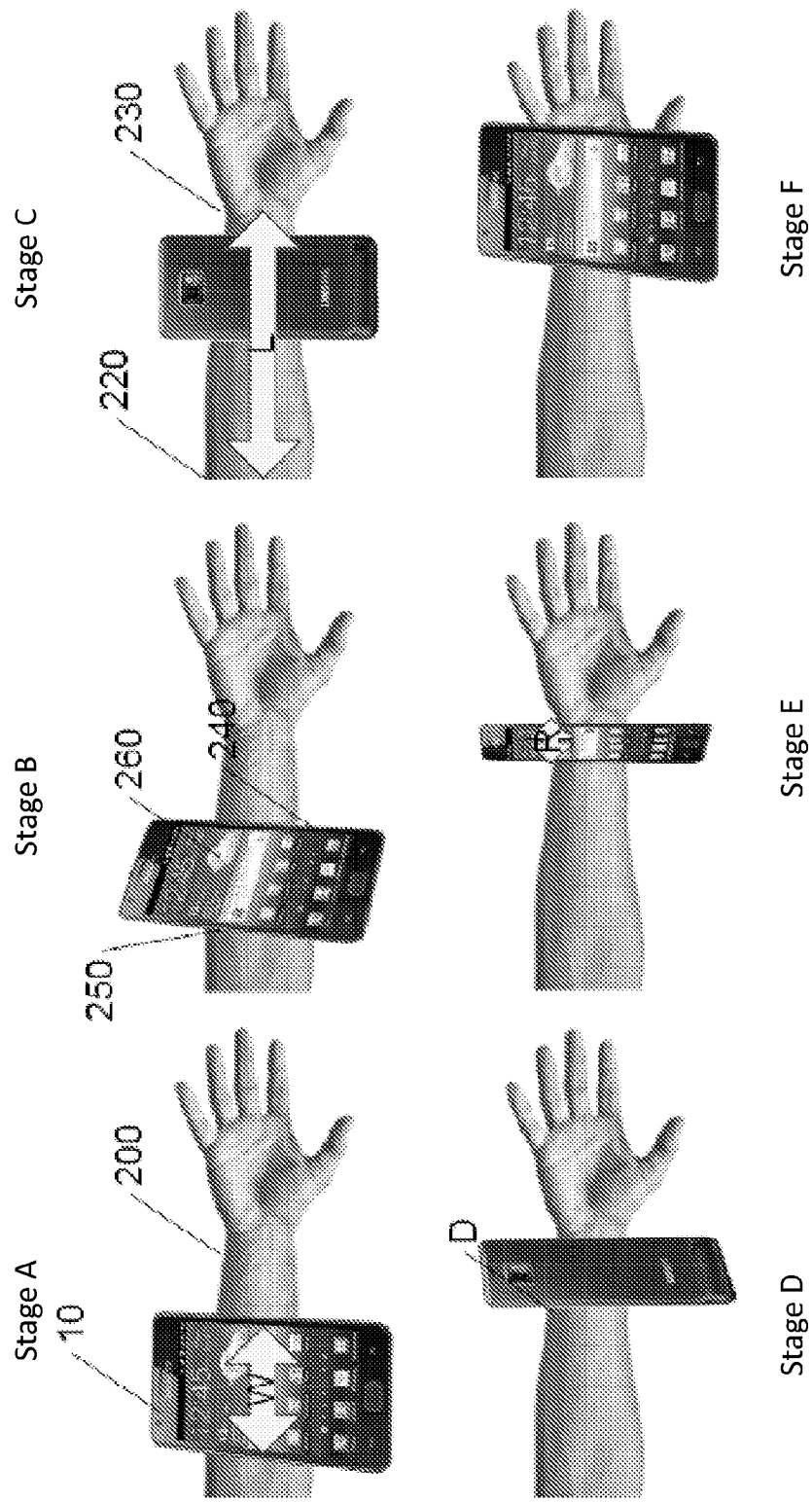
Figure 4:
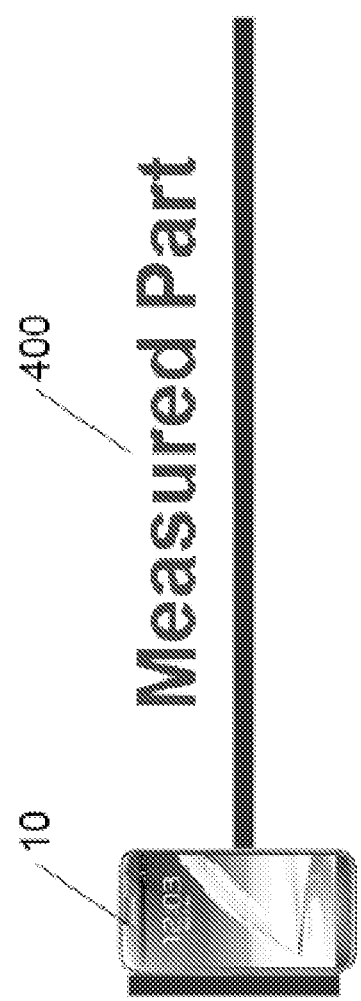

In order to understand the presently disclosed subject matter and to see how it may be carried out in practice, the subject matter will now be described, by way of non-limiting examples only, with reference to the accompanying drawings, in which:

FIG. 1 is a schematic representation of an example of a device for use by a user to measure a path length using a continuous rotation;

FIGS. 2A-2C are schematic illustrations of a method for measuring a path length using a handheld electronic device;

FIG. 3A-3D depicts the calculation of a measured length for a surface, according to an example; and, FIG. 4 is a schematic illustration of a method to obtain a path length.

DETAILED DESCRIPTION

In the following detailed description, numerous specific details are set forth in order to provide a thorough understanding of the methods and apparatus. However, it will be understood by those skilled in the art that the present methods and apparatus may be practiced without these specific details. In other instances, well-known methods, procedures, and components have not been described in detail so as not to obscure the present methods and apparatus.

Although the examples disclosed and discussed herein are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method examples described herein are not constrained to a particular order or sequence. Additionally, some of the described method examples or elements thereof can occur or be performed at the same point in time.

Unless specifically stated otherwise, as apparent from the following discussions, it is appreciated that throughout the specification, discussions utilizing terms such as "adding", "associating" "selecting," "evaluating," "processing," "computing," "calculating," "determining," "designating," "allocating" or the like, refer to the actions and/or processes of a computer, computer processor or computing system, or similar electronic computing device, that manipulate, execute and/or transform data represented as physical, such as electronic, quantities within the computing system's registers and/or memories into other data similarly represented as physical quantities within the computing system's memories, registers or other such information storage, transmission or display devices. Unless specifically stated otherwise, as apparent from the following discussions, it is appreciated that throughout the specification discussions utilizing terms such as "obtaining", "determining", "comparing" or the like, include actions and/or processes of a computer processor that manipulate and/or transform data into other data, said data represented as physical quantities, e.g. such as electronic quantities, and/or said data representing the physical objects.

The term "computer", "computer processor", "processor" or the like should be expansively construed to cover any kind of electronic device with data processing capabilities, including, by way of non-limiting example, a personal computer, a server, a computing system, a communication device, a processor (e.g. digital signal processor (DSP), a microcontroller, a field programmable gate array (FPGA), an application specific integrated circuit (ASIC), etc.), any other electronic computing device, and or any combination thereof.

Examples of the present invention may include apparatuses for performing the operations described herein. Such apparatuses may be specially constructed for the desired purposes, or may comprise computers or processors selectively activated or reconfigured by a computer program stored in the computers. Such computer programs may be stored in a computer-readable or processor-readable non-transitory storage medium, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions. It will be appreciated that a variety of programming languages may be used to implement the teachings of the invention as described herein. Examples of the invention may include an article such as a non-transitory computer or processor readable non-transitory storage medium, such as for example, a memory, a disk drive, or a USB flash memory encoding, including or storing instructions, e.g., computer-executable instructions, which when executed by a processor or controller, cause the processor or controller to carry out methods disclosed herein. The instructions may cause the processor or controller to execute processes that carry out methods disclosed herein.

The operations in accordance with the teachings herein may be performed by a computer specially constructed for the desired purposes or by a general purpose computer specially configured for the desired purpose by a computer program stored in a computer readable storage medium.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus the appearance of the phrase "one case", "some cases", "other cases" or variants thereof does not necessarily refer to the same embodiment(s).

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

It is to be understood that the system according to the presently disclosed subject matter may be a suitably programmed computer. Likewise, the presently disclosed subject matter contemplates a computer program being readable by a computer for executing the method of the presently disclosed subject matter. The presently disclosed subject matter further contemplates a machine-readable memory tangibly embodying a program of instructions executable by the machine for executing the method of the presently disclosed subject matter.

It is also to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the present presently disclosed subject matter.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

FIG. 1 is a schematic representation of an example of a handheld electronic device (also referred to simply as a device) for use by a user to measure a path length using a continuous rotation (also referred to as tumbling).

In some examples, a user may measure a path length of a body part. For example, the user may measure a leg length, an arm length or a distance between shoulders. The measurement may be applicable for online commerce, e-commerce, m-commerce and/or other forms of Internet based commerce. The measurement may be applicable for brick and mortar based commerce. The measurement may be applicable for three-dimensional printing. The measurement may be applicable for other uses relating to the body, including commercial, medical, cosmetic and/or other uses.

In some examples, the user may measure a path length of an item using a continuous rotation. For example, the presently disclosed method may be performed over a garment, for example to measure a sleeve's length. In some examples, a user may measure a path length of a body part using a continuous rotation. In some examples, the device may be a smartphone configured to measure said path length by counting how many revolutions (360 degrees rotation) of the handheld electronic device were necessary to cover the path length. In some embodiments, a revolution of the handheld electronic device may be divided in fractional increments (or sectors) and the handheld electronic device may be configured to count the fractional increments of revolution.

In some examples, a handheld electronic device 10 may have one or a plurality of sensors 20 configured to measure rotation. In some examples, device 10 may have one or a plurality of sensors configurable to measure rotation. The one or plurality of sensors 20 may be capable of (and/or configured for) continuously sensing a rotational change (i.e. orientation variation) of the handheld electronic device. The one or a plurality of sensors may include positioning sensors, gyroscopes, motion sensors, accelerometers, ambient light sensors, moisture sensors, proximity sensors, magnetometer, compass, and/or other sensors. The one or a plurality of sensors 20 and/or other internal components, units, external components and/or parts may be configured and/or configurable to measure, characterize and/or provide data related to a path length.

Device 10 may include one or a plurality of processors 30. The one or a plurality of processors 30 may be configured to measure rotation and to calculate data related to said rotation and said path length. The one or a plurality of processors 30 may be configured to measure rotation and to calculate data related to said rotation and said path length.

Device 10 may have one or a plurality of outputs. Outputs may include screen 40. The screen 40 may be a touch screen capable of receiving user inputs. Outputs may include data transfer ports and/or other outputs. Screen 40 and data transfer ports may be used for inputs. In some examples, device 10 may have wireless, cellular, Bluetooth, and/or other forms of over air, wireless connectivity. Device 10 may be configured and/or configurable for wired connectivity.

Device 10 may include one or a plurality of power sources 50. Power source 50 may be a battery, solar cell, an input for external power, and/or other sources of power to supply power to device 10.

Device 10 may include one or a plurality of memory 60. The one or a plurality of memory may include solid state and/or other forms of storage. One or a plurality of memory 60 may include SIM cards and/or storage slots.

Device 10 may include one or more non-transitory computer-readable media storing computer-readable instructions 70 that, when executed by device 10 or a component therein, cause device 10 to implement various functions of the electronic device including software for implementing the method for measuring a path length according to the present disclosure. The non-transitory computer-readable media storing computer-readable instructions 70 may include software, including firmware, operating systems, programs, applications (apps), widgets, and/or other software. The software may be stored locally, on a network, in the cloud and/or in another storage location.

Device 10 may include one or a plurality of cameras, including for example, still cameras and video cameras and/or other image input devices configurable to capture image input.

FIG. 2A is a schematic illustration of a method for measuring a path length using a continuous rotation.

In some examples, a user may rotate a device, e.g., device 10 described hereinabove, over an item to measure a path length. As previously explained, the rotation of the device 10 may be performed as a repeated forward tumbling of the handheld electronic device over the path to be measured. More precisely, the handheld electronic device may be repeatedly pivoted forward around its forward bottom edge, wherein a bottom orientation may be defined with respect to the path surface and a forward orientation may be defined with respect to the path direction.

In some examples, a user may rotate a device over a body part 200 to measure a path length L. Path length L includes a proximal edge 220 and a distal edge 230. In some examples, path length L may include a remaining path length R.

In some examples, the device may be rotated over path length L by a third party to measure a body part. In some examples, the device may rotate over path length L to measure a body part. In some examples, the device may otherwise characterize body part 200.

Device 10 may be configured to measure, calculate, and/or otherwise compute the length to of body part 200.

The device 10 may substantially have a rectangular cuboid shape. As explained above, a height H, width W and thickness T of the handheld electronic device may therefore be defined. Device 10 may have a distal edge 240 and a proximal edge 250 separated by the width W. In some examples, distal edge 240 and proximal edge 250 may be absolutely defined in relation to device 10. For example distal edge 240 may be the sinister side of device 10 when device 10 is oriented with a primary screen 260 of device 10 toward the user, and proximal edge of device 10 may be the dexter side of device 10 when primary screen 260 of device 10 is oriented toward the user.

In some examples, distal edge 240 and proximal edge 250 are relative to the user, where the distal edge is an edge oriented on a far side of device 10 in relation to the user, when device 10 is positioned to measure path length and proximal edge is an edge oriented to a near side of device 10, in relation to the user, when device 10 is positioned to measure path length.

A user may roll (tumble) device 10 over body part 200 as illustrated starting from A through F in FIG. 2A. For example, a starting position of the device 10 may be such that a bottom face of the device (parallel to the face supporting the screen) contacts the path to be measured with a distal edge 240 in the forward direction. The distal edge 240 may be perpendicular to the forward direction (path direction). Furthermore, the starting position may be such that either the distal edge 240 (also referred to as distal starting position configuration) or the proximal edge 250 (also referred to as proximal starting position configuration) reaches a beginning of the path to measure. In other words, there might be two starting position configurations in which an edge of the handheld electronic device reaches the beginning of the path to be measured: a distal starting position configuration in which the handheld electronic device does not cover the path to be measured; and a proximal starting position configuration in which the handheld electronic device already covers a part of the path to be measured. The handheld electronic device may be configured so as to be informed of the starting position configuration to properly calculate the path length, for example through a menu in a graphical interface.

FIG. 2B provides another illustration of the tumbling movement. As can be seen in FIG. 2B, starting from a proximal starting position configuration in which a face F0 of the handheld electronic device 10 lays on the path to be measured, the handheld electronic device is pivoted around its forward bottom edge 270 so that a successive rolling face F1 covers the path to be measured. In this movement, the forward bottom edge 270 forms a rotation axis A. As can be seen, the tumbling movement may preferably avoid a slipping of the device 10 when the device is pivoted around edge 270 i.e. the forward bottom edge 270 may not be translated while the device rotates. The forward direction may be defined with respect to a path direction D and the bottom direction may be defined with respect to a path surface S. The repeated tumbling may be carried out until a projection of an edge of the handheld electronic device 10 reaches an end of the path to be measured.

Returning to FIG. 2A, the rolling and/or rotation of the device may be a complete rotation over a portion of the path length of the body part. The rolling and/or rotation of the device may be an incomplete (partial) rotation over a portion of the path length of the body part. A processor, for example the processor described above, may take one or more measurements with regard to an angle of device 10 with reference to body part 200 in Stage A. Said processor, or another processor may take one or more measurements with regard to an angle of device 10 with reference to body part 200 in Stage F. Said processor may be configured to determine the completion and/or incompletion of a rotation (revolution) of the device over the body part.

In some examples, while the device rotates or rolls along a length of body part 200, a projection of an edge of the phone may reach the end of the measured length of said body part. The processor may take into account an incomplete final roll to calculate the path length as a function of said projection.

In some examples, a method of rotating device 10 may be configured to count coarse units of measurement via counting for example, the number of rotations (revolutions) from Stage A through Stage F. Device 10 may be configured to calculate a length at the end of said rotations, e.g., at stage F with less coarse units of measurement, for example, when the path length to be measured is not a whole number or integer multiple of the length of a complete rotation of device 10, e.g., when measuring the path length requires one or more full rotations of device 10 and a partial and/or incomplete rotation of device 10. For example said less coarse units of measurements may be a fraction of the perimeter of device 10. In some examples, device 10 of perimeter 16.0 cm may result in less coarse units of 2.0 cm each. In some examples, a method of rotating device 10 may use coarse measurements of less than or greater than 2.0 cm.

In some examples, said method may enable depth measurements and may be used to measure non-straight and/or curving surfaces such as the human breast, for example, for use in e-commerce.

In some examples, the start and the end of the rotation may be voice controlled, in order that the user to focus on the tumbling movement of the phone. Voice controls may further serve to limit said user from touching unnecessary controls on the screen.

The handheld electronic device may be configured to count fractional increment of revolution with respect to a reference position. In some examples, a revolution may be divided into a plurality of sectors (fractional increment of revolution), for example 16. The handheld electronic device 10 may be configured to sense a rotational change of the handheld electronic device using for example a gyroscope and/or accelerometers. Based on a sensed rotational change, the handheld electronic device may determine which sectors have been traversed during the tumbling movement. For example a rotation of 360 degrees, (i.e. two flips of said device, each flip of 180 degrees) may be divided into 16 sectors such that each partial rotation of 22.5 degrees traverses a sector. The cumulative sectors and/or the traverse of all of said sectors may provide an assessment of the angle of rotation of the device. In some examples, the 360 degrees of rotation may be divided into a greater or lesser number of sectors.

In some examples, a full rotation may be divided into 32 sectors, each sector representing a partial rotation of 11.25 degrees.

In some examples, the rotation may represent greater or less than 180 degrees, and/or greater or less than 360 degrees.

The 16 sectors may be monitored by a counter. The counting of the sectors (fractional increments of revolution) may include updating the counter. The counter may comprise a 16 bit array: e.g., 0000000000000000; each bit corresponding to a sector, in an ascending order. In some examples, said 16 sectors may be represented by an array of a factor of 16, for example a 32 bit or a 160 bit array. In some examples, n sectors may be represented by an xn bit array where x and n are whole numbers and where xn is a multiple of n.

At the initialization stage, e.g., prior to beginning the first and/or the nth rotation, the array has only 0's: 0000000000000000.

When device 10 completes the rotation of a sector, and/or enters a new sector, e.g., after rotating 22.5 degrees, the corresponding bit of that sector is flipped to a 1.

For example, after a first rotation the array may be represented as: 1000000000000000.

After a rotation through a second sector said array may be represented as: 1100000000000000.

After a rotation through the 16th array, e.g., after rotating a full 360 degrees and/or after completing a full rotation, the array may be represented as 1111111111111111.

Said one or more processors will read array the 1111111111111111 as the completion of a full rotation. In some examples, said completion of a full rotation represents a length measurement equal to the perimeter of the device, e.g., the sum of two widths and two depths of the device, for example, as described above. In some examples, said completion of a rotation may represent a length measurement equal to another value related to the device, e.g., a factor or one or a plurality of the device's dimensions.

In some embodiments, each fractional increment of revolution (sector) may be associated with a corresponding perimeter projection part so that completion of each sector can be associated with an incremental path measurement. The association of the perimeter projection parts with the sectors may depend on a tumbling movement configuration. A tumbling movement configuration may be defined based on the direction of the rotation axes of the successive rotations with respect to the handheld electronic device i.e. on whether the axis of the successive rotations are perpendicular to a width section plane (width tumbling), to a height section plane (height tumbling) or to a thickness section plane (thickness tumbling) of the handheld electronic device. The perimeter projection parts may be determined using geometric relations such as Pythagorean, trigonometric and other methods. For example, as illustrated in FIG. 2C, for a sector within 0° and 90°, the perimeter projection part may be expressed by:

$$p_i = d * \cos\left(\frac{\pi}{2} - \theta\right) - p_{i-1}$$

Wherein:

$p_i$ is the perimeter projection part associated with the i'th sector, d is an extension (width, length or thickness) of a face F1 brought on the path with respect to a direction perpendicular to a rotation axis of the device, θ is an angle of rotation of the device when passing the i'th sector, and $p_0$ is equal to 0.

In some examples, an inaccurate sensor, device and/or user, and/or a user error may lead to the skipping and/or non-detection of one or more sectors and/or the rotation through said sector. Said one or a plurality of processors may be configured to self-correct missed and/or skipped sectors.

In some examples, a sensor that erroneously or otherwise skips or does not sense a rotation of a sector may self-correct that skip. For example, a 16 bit array as described above that reads 1101100000000000, where the bolded zero is likely an erroneously non-sensed portion of a continuous rotation through at least 5 sectors will be automatically, semi-automatically and/or manually corrected to read: 1111100000000000 (emphasis added).

In some examples, heuristics can be applied to determine when a sector has been skipped purposely, erroneously and/or otherwise and in some examples, correct said skipping. Said skipping may be the result of a user manipulating said device incorrectly, too quickly and/or the result of other actions by said user, a third party or said device or a failure or partial failure of the device and/or a component thereof.

These heuristics include:

Heuristic A: Given the sequence 1101—the 0 will be turned on—if we passed two sectors before and one in front, we can assume that we skipped a sector.

Heuristic B: Given the sequence 1011—the 0 will be turned on—if two sectors in front and one before are passed, it can be assumed that a sector has been skipped.

Heuristic C: Given the sequence 11100111—the front 0 will be turned on—if three sectors in front and three before are passed, it can be assumed that a sector has been skipped.

FIG. 3 depicts the calculation of a measured length for a surface, according to an example.

In some examples, as explained above, a device, for example the device 10 described hereinabove, e.g., a smartphone, may be used by a user to measure a path length wherein said path length is not an integer multiple of the width of the device and or a sum of one or a plurality of dimensions of said device e.g., said length cannot be factored by the width of said device, and or a sum of one or a plurality of dimensions of said device and a whole number.

In some examples, a path length of an item may be equal to a whole number multiple of the width of the device, and a remaining path length, wherein measuring said remaining path length would correspond to and/or entail a partial rotation of the device over said path length, e.g., a partial final rotation that would correspond to a rotation of less than 180 degrees or a rotation of between 180 degrees and 360 degrees.

In completing a partial final rotation over a remaining path length, for example as described above, a user may, in some examples, project a distal edge of the width of said device, e.g., the distal edge as described above over the remaining path length of at the distal edge (end) of the path length, e.g., the distal edge of the path length as described above. In some examples device 10 may project a beam of light such that such beam aligns with the distal edge of the path length during an incomplete rotation, and such that the distal edge of the device may be projected accurately or nearly accurately over said distal edge of the path length. In some examples, device 10 may determine where a straight-line, representable in some examples by a beam of light, would project and calculate angles and distances based on the determined projection of said beam of light.

In some examples, the calculation for determining said path length that includes a remainder path length may be dependent on extraneous factors. In some examples said calculation may include factoring in a slope of the item.

In FIG. 3A the calculation of the path length may include the addition of the remaining path length to the path length calculated up until and including a penultimate rotation or portion thereof.

In FIG. 3B the calculation of a path length includes the path length calculated up until and including the penultimate rotation or part thereof and the remainder, wherein the remainder may be calculated by determining an angle of rotation of the device, the angle of rotation may be determined from an array, e.g., the array described above, wherein the angle of rotation is equal to the number of sectors in the 16 bit array that are read as a 1 multiplied by the degrees that are encompassed within each sector. Using a Pythagorean and/or other methods, said angle of rotation can be used to calculate the remaining path length, wherein said remaining path length is added to the calculated path length up until and including the penultimate rotation or portion thereof to determine the total path length of an item, e.g., a body part as described hereinabove. An analysis of the data from a partial rotation may result in a length value that may be between 25% to 75% of the width of the device.

In FIG. 3C a calculation of the path length includes a calculation of only completed rotations, but not partial rotations.

In FIG. 3D a calculation of an entire path length includes the path length calculated up until and including the penultimate rotation or part thereof and a remaining path length, wherein the remaining path length may be calculated using a Pythagorean and/or other methods as described above. In some examples, a correction factor may be included when said path length extends along a surface that is not flat or nearly flat.

In some examples, a sensor within the device may be used to determine whether the surface of the item to be measured is flat, and if not, what is the slope, tilt, incline, elevation and/or depression of said item. In some examples, the device may include sensors such as inclinometers, clinometers, and/or other sensors to measure whether a surface is flat and or inclined. This data may be used to calculate the remaining path length in some examples.

FIG. 4 is a schematic illustration of a method to obtain a path length.

In some examples, a path length e.g., measured part 400 of an item may be determinable from a number of full rotations of a device 10 and a final angle of rotation of a partial and/or incomplete rotation.

In some examples, a user may place device 10 within the path length to begin the measuring process. In some examples, a user may place device 10 outside of a path length to begin the measuring process (also referred to as distal starting position configuration).

Given the sum of whole number of rotations: "fullRotation" and the sum of the partial Rotations "partRotation" the length of the corresponding path's length may be calculated as follows:

$$pathLength = rotationLength(N) + partRotation$$

Where:
pathLength is the measured length of the item measured;
rotationLength is the traversed path of the rotating device;
N is the number of full rotations of the device over said traversed path;
partRotation is a function related to the degrees rotation of a partial rotation of the device, for example the number of sectors included within said partial rotation.

In some examples pathLength may be calculated by summing all sectors of all full and partial and/or incomplete rotations and applying that sum to an algorithm.

In some examples, rotationLength may depend on whether the device is positioned in the starting position within the desired measured path or outside the desired measured path.

In some examples involving a width tumbling movement, where a full rotation is 360 degrees, a rotation length of the device where the device is first situated outside measured path (distal starting position configuration), may be computed as:

$$rotationLength = 2W + 2D$$

Where W is the width of said device and D is the depth of the device, for example, as described above. Thus the rotationLength may be a sum of the span of two widths of the device added to the sum of two depths of the device. In some examples, a user may be able to input the values of the width and the depth. In some examples, the device's width and/or depth may be computed automatically. In some examples, the device's width and/or depth may be computed automatically, taking into account the brand and model of the device and/or any additional packaging on the device, e.g., a protective case. In some examples rotationLength may be the sum of one or a plurality of dimensions of the device. In some examples, rotationLength may be related to the sum of one or a plurality of dimensions of the device, for example a multiple thereof.

In some examples involving a width tumbling movement, where a full rotation is 360 degrees and the device is first situated inside of the measured path length (proximal starting position configuration), a first rotation length may be calculated as:

For the first rotation, calculate:

$$rotationLength_1 = 3W + 2D$$

For 1+n, e.g., all subsequent rotations, calculate:

$$rotationLength_{1+n} = 2W + 2D$$

To get the total measured path length calculate:

$$pathLength = rotationLength_1 + rotationLength_{1+n}(N) + \int partRotation$$

It is to be understood that the system according to the presently disclosed subject matter may be a suitably programmed computer. Likewise, the presently disclosed subject matter contemplates a computer program being readable by a computer for executing the method of the presently disclosed subject matter. The presently disclosed subject matter further contemplates a machine-readable memory tangibly embodying a program of instructions executable by the machine for executing the method of the presently disclosed subject matter.

It is also to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the present presently disclosed subject matter.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for measuring a path length using a handheld electronic device comprising:
   repeatedly tumbling forward the handheld electronic device so as to cover the path to be measured;
   sensing a rotational change of the handheld electronic device during the tumbling of the handheld electronic device;
   determining whether a fractional increment of revolution of the handheld electronic device has been traversed based on the sensed rotational change;
   counting the fractional increments of revolution of the handheld electronic device with respect to a starting position;
   determining an error in the counted fractional increments of revolution;
   correcting the error in the counted fractional increments of revolution; and
   estimating the path length based on the corrected counted fractional increments of revolution.

2. The method according to claim 1, wherein each fractional increment is associated with a corresponding perimeter projection part of the handheld electronic device and the path length is estimated by summing said perimeter projection parts.

3. The method according to claim 1, wherein a revolution of the handheld electronic device is divided into a predetermined number of fractional increments and wherein counting the fractional increments comprises updating a counter comprising a bit array of a corresponding predetermined number of bits.

4. The method according to claim 1, wherein the sensing of the rotational change is performed repeatedly while the handheld electronic device is tumbled forward.

5. The method according to claim 2, wherein the perimeter projection parts are based on an extension of the handheld electronic device in a section plane perpendicular to a rotation axis of the handheld electronic device.

6. The method according to claim 1, further comprising detecting a slipping movement of the handheld electronic device based on the sensed rotational change and correcting the estimated path length using the detected slipping.

7. The method according to claim 1, wherein the fractional increments of revolution correspond to a rotation of the handheld electronic device of 22.5 degrees each.

8. The method according to claim 1, wherein a user conducts said method via voice commands.

9. The method according to claim 1, wherein said handheld electronic device is a smartphone.

10. The method according to claim 1, wherein said path is a body part.

11. The method according to claim 2, wherein the sum of the perimeter projection parts corresponding to a revolution of the handheld electronic device approximates a perimeter of a section of the handheld electronic device in a plane perpendicular to a rotation axis direction.

12. The method according to claim 1, wherein the measuring of a path length using a handheld electronic device is configurable for use in e-commerce.

13. The method according to claim 1, wherein the sensing of the rotational change is performed continuously.

14. One or more non-transitory computer-readable media storing computer-readable instructions that, when executed by a handheld electronic device repeatedly tumbled forward so as to cover a path to be measured, cause the handheld electronic device to measure the path length by:
   sensing a rotational change of the handheld electronic device during the tumbling of the handheld electronic device;
   determining whether a fractional increment of revolution of the handheld electronic device has been traversed based on the sensed rotational change;
   counting the fractional increments of revolution of the handheld electronic device with respect to a reference position;
   determining an error in the counted fractional increments of revolution;
   correcting the error in the counted fractional increments of revolution; and
   estimating the path length based on the corrected counted fractional increments of revolution.

15. The one or more non-transitory computer-readable media storing computer-readable instructions of claim 14, wherein each fractional increment is associated with a corresponding perimeter projection part of the handheld electronic device and the path length is estimated by summing said perimeter projection parts.

16. The one or more non-transitory computer-readable media storing computer-readable instructions according to claim 14, wherein a revolution of the handheld electronic device is divided into a predetermined number of fractional increments and wherein counting the fractional increments comprises updating a counter comprising a bit array of a corresponding predetermined number of bits.

17. The one or more non-transitory computer-readable media storing computer-readable instructions according to claim 14, further comprising instructions for detecting a slipping movement of the handheld electronic device based on the sensed rotational change and correcting the path length estimated based on the detected slipping.

18. The one or more non-transitory computer-readable media storing computer-readable instructions according to claim 14, wherein the sensing of the rotational change is performed repeatedly while the handheld electronic device is tumbled forward.

19. The one or more non-transitory computer-readable media storing computer-readable instructions of claim 14, wherein the fractional increments of revolution correspond to a rotation of the handheld electronic device of 22.5 degrees each.

20. The one or more non-transitory computer-readable media storing computer-readable instructions of claim 14, further causing the handheld electronic device to respond to voice commands to measure a path length.

21. The one or more non-transitory computer-readable media storing computer-readable instructions of claim 14, configurable to run on a smartphone.

22. The one or more non-transitory computer-readable media storing computer-readable instructions of claim 14, configurable to measure a body part.

23. The one or more non-transitory computer-readable media storing computer-readable instructions of claim 14, configurable to be used in e-commerce.

24. A system for measuring a measuring a path length comprising:
   a handheld electronic device being intended to be tumbled forward so as to cover a path length to be measured, the handheld electronic device comprising:
      one or a plurality of sensors capable of sensing a rotational change of the handheld electronic device; and one or a plurality of processors configured for:
- sensing a rotational change of the handheld electronic device using the one or plurality of sensors during the tumbling of the handheld electronic device;
- determining whether a fractional increment of revolution of the handheld electronic device has been traversed based on the sensed rotational change;
- counting the fractional increments of revolution of the handheld electronic device with respect to a starting position;
- determining an error in the counted fractional increments of revolution;
- correcting the error in the counted fractional increments of revolution; and
- estimating the path length based on the corrected counted fractional increments.

25. The system according to claim 24, wherein each fractional increment is associated with a corresponding perimeter projection part of the handheld electronic device and estimating the path length is performed by summing said perimeter projection parts.

26. The system according to claim 24, further configured for detecting a slipping movement of the handheld electronic device based on the sensed rotational change and correcting the path length estimated based on the detected slipping.

27. The system according to claim 24, wherein the sensing of the rotational change is performed repeatedly while the handheld electronic device is tumbled forward.

28. The system of claim 24, wherein said one or a plurality of processors is configured to automatically perform a correction of the counted fractional increments.

29. The system of claim 24, wherein the fractional increments of revolution correspond to a rotation of the handheld electronic device of 22.5 degrees each.

30. The system of claim 24, wherein said one or a plurality of processors is configured for responding to voice commands.

31. The system of claim 24, wherein said one or a plurality of sensors and said one or a plurality of processors are in a smartphone.

32. The system of claim 24, configurable to measure a body part.

33. The system of claim 24, configurable to be used in e-commerce.

34. A method for measuring a path length using a continuous rotation comprising:
- sensing at least a first rotation of a device along a path length;
- dividing the at least first rotation of the device into sectors, each sector being a portion of an angle of rotation of the device, wherein the sum of all traversed sectors at least approximate the angle of rotation of the device;
- counting said sectors to determine a completion of the at least first rotation wherein a full rotation of the device represents a measurement, said measurement at least approximating a length, the length equal to a multiple of a width and a multiple of a depth of the device;
- and/or counting said sectors to calculate an incompletion of the at least first rotation or a subsequent rotation wherein an incomplete rotation represents a measurement less than the measurement represented by the full rotation and wherein said measurement less than the measurement represented by the full rotation is calculated as a function of the angle of rotation;
- determining an error in the counted sectors;
- correcting the error in the counted sectors; and
- calculating the path length based on the corrected counted sectors by summing the measurements represented by the full rotations of the device and the measurements represented by the incomplete rotations of the device.

35. A computer program product adapted to perform the method of claim 34.

36. The method according claim 3, further comprising correcting the bit array according to the determined error.

37. The method according to claim 1, further comprising applying a heuristic to determine the error in the counted fractional increments of revolution.

* * * * *